(12) United States Patent
Tsubooka et al.

(10) Patent No.: US 8,808,238 B2
(45) Date of Patent: Aug. 19, 2014

(54) METHOD OF MANUFACTURING BALLOON CATHETER AND BALLOON CATHETER

(75) Inventors: Michiyo Tsubooka, Fujinomiya (JP); Takako Matsuno, Fujinomiya (JP); Yuichi Tada, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 13/294,408

(22) Filed: Nov. 11, 2011

(65) Prior Publication Data
US 2012/0059317 A1   Mar. 8, 2012

Related U.S. Application Data

(63) Continuation of application No. PCT/JP2010/057033, filed on Apr. 21, 2010.

(30) Foreign Application Priority Data

May 14, 2009   (JP) .................................. 2009-117317

(51) Int. Cl.
*A61M 25/10*   (2013.01)
(52) U.S. Cl.
USPC .............. 604/103.06; 604/103.7; 604/103.08; 604/103.14

(58) Field of Classification Search
USPC .............. 604/96.01, 103.02, 103.07, 103.08, 604/103.14, 103.06
See application file for complete search history.

(56) References Cited

U.S. PATENT DOCUMENTS 5,693,014 A   12/1997   Abele et al.
8,226,603 B2 *   7/2012   Von Oepen et al. ..... 604/103.05

FOREIGN PATENT DOCUMENTS

| | | |
|---|---|---|
| JP | 8-024328 A | 1/1996 |
| JP | 2003-117002 A | 4/2003 |
| JP | 2005-224635 A | 8/2005 |

OTHER PUBLICATIONS

International Search Report (PCT/ISA/210) issued on Jul. 6, 2010, by Japanese Patent Office as the International Searching Authority for International Application No. PCT/JP2010/057033.

* cited by examiner

*Primary Examiner* — Laura Bouchelle

(57) ABSTRACT

A method of manufacturing a balloon catheter involves applying a first application liquid, which contains a hydrophilic coating material, to the outer periphery of a balloon which is disposed on an elongated catheter and is held in an expanded state; folding the balloon; and applying a second application liquid, which contains the hydrophilic coating material, to the balloon with the balloon folded.

12 Claims, 4 Drawing Sheets

METHOD OF MANUFACTURING BALLOON CATHETER AND BALLOON CATHETER

This application is a continuation of International Application No. PCT/JP2010/057033 filed on Apr. 21, 2010, and claims priority to Japanese Application No. 2009-117317 filed on May 14, 2009, the entire content of both of which is incorporated herein by reference.

TECHNOLOGICAL FIELD

The present invention generally relates to a balloon catheter and a method of manufacturing a balloon catheter.

BACKGROUND DISCUSSION

Various medical procedures, for example PTA (percutaneous transluminal angioplasty) and PTCA (percutaneous transluminal coronary angioplarsty), utilize a balloon catheter provided with an expandable and contractible balloon.

Such a balloon catheter is used by inserting the balloon catheter into a blood vessel from outside a living body, and, when the balloon has reached a stenosed part of the blood vessel serving as a target site, the balloon is expanded to expand the stenosed part. Since blood vessels into which the balloon catheter is inserted are generally accompanied by a sharp bend, stenosis or the like, the balloon catheter must exhibit low-friction properties, trackability, anti-kinking properties, etc. To enhance, by way of example, the low-friction properties, the catheter, particularly the balloon and the catheter body inserted into a blood vessel, are coated with a hydrophilic material or the like. An example of this is described in Japanese Patent Laid-open No. Hei 8-24328.

In the conventional balloon catheters coated with a hydrophilic material, however, the coating of the hydrophilic material is susceptible to peeling. For example, because the balloon is folded into a small-sized form after the coating step, the coating may undergo exfoliation, leading to a lowered operationality.

SUMMARY

The balloon catheter disclosed here facilitates a reduction in the sliding resistance of the balloon so that the sling resistance is relatively low, and exhibits excellent operationality. The balloon catheter manufacturing method disclosed here makes it possible to produce a balloon catheter having desirable characteristics.

A method of manufacturing a balloon catheter involves applying a first application liquid, which contains a hydrophilic coating material, to the outer periphery of a balloon which is disposed on a catheter, with the first application liquid being applied while the balloon is in an expanded state, folding the balloon, and applying a second application liquid, which contains a hydrophilic coating material, to the balloon while the balloon is folded.

In addition, in the method of manufacturing the balloon catheter, the first application liquid and the second application liquid are applied under different conditions.

The content of the hydrophilic coating material in the first application liquid is preferably lower than the content of the hydrophilic coating material in the second application liquid.

In addition, the method of manufacturing the balloon catheter preferably involves satisfying the relationship $1<X2/X1\leq100$, where X1 [wt %] is the content of the hydrophilic coating material in the first application liquid and X2 [wt %] is the content of the hydrophilic coating material in the second application liquid.

The method of manufacturing the balloon catheter can also involve carrying out the application of the first and second application liquids by dipping, with the rate of pulling up the balloon from the first application liquid being lower than the rate of pulling up the balloon from the second application liquid in the second application step.

The method of manufacturing the balloon catheter can also be performed to satisfy the relationship $1<V2/V1\leq20$, where V1 [mm/sec] is the rate of pulling up the balloon from the first application liquid and V2 [mm/sec] is the rate of pulling up the balloon from the second application liquid, is satisfied.

Another aspect involves a balloon catheter manufactured by the manufacturing method.

The balloon catheter includes a catheter, and a balloon disposed on the catheter, wherein the balloon has a first hydrophilic coating layer on an outer surface thereof, and has a second hydrophilic coating layer surrounding the periphery of the balloon in the state of being folded in such a manner as to be wrapped around the catheter.

The balloon catheter is preferably configured such that a fold of the balloon, which is in the folded state, overlaps with other part of the balloon, and the second hydrophilic coating layer is so provided as to extend across a boundary between the fold and the other part.

In addition, the thickness of the first hydrophilic coating layer is preferably smaller than the thickness of the second hydrophilic coating layer.

The balloon is preferably folded so as to be wrapped around the outer periphery of the catheter.

The method of manufacturing the balloon catheter preferably involves applying the first application liquid and the second application liquid by a method selected from the group consisting of dipping and spraying.

The method of manufacturing the balloon catheter preferably, further includes cleaning the part coated with the first application liquid by use of a cleaning liquid, with the balloon expanded, between the first application step and the folding step.

In addition, the method of manufacturing the balloon catheter according to the present invention, preferably, further includes a heating step for mounting the balloon catheter to a member for maintaining the folded state of the balloon and subjecting the balloon in this state to a heating treatment, between the folding step and the second application step.

BRIEF DESCRIPTION OF THE DRAWING FIGURES

Figure 4:
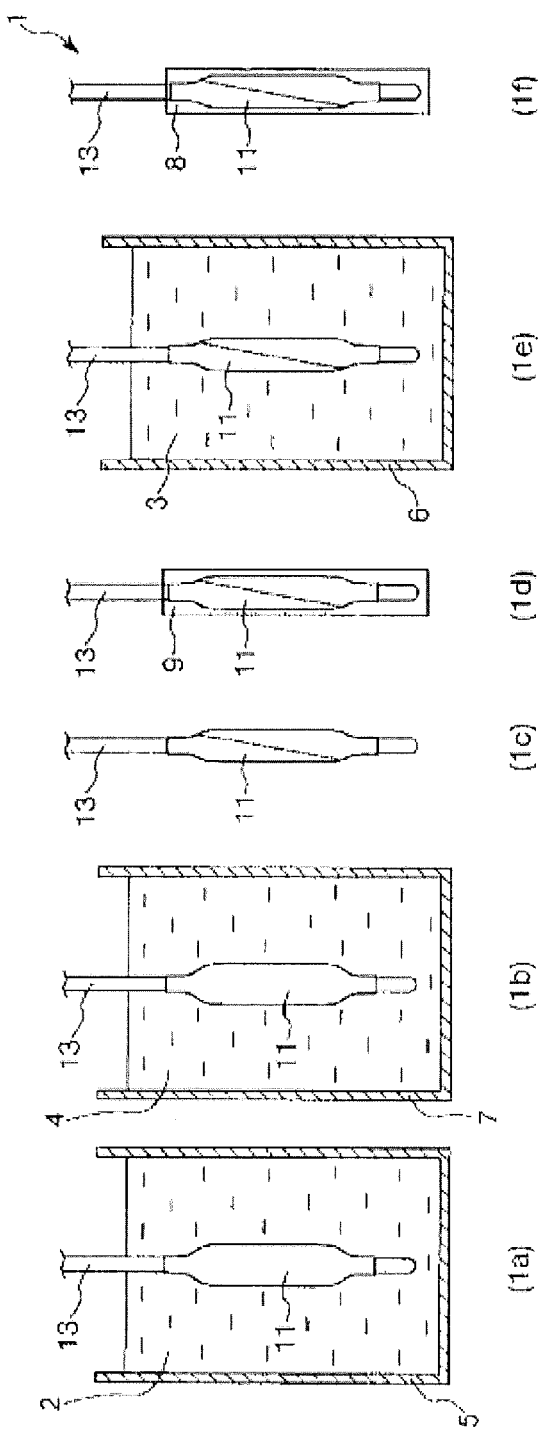

FIG. 4 schematically shows steps associated with one example of a method of manufacturing a balloon catheter accordance with the disclosure here

DETAILED DESCRIPTION

Figure 1:
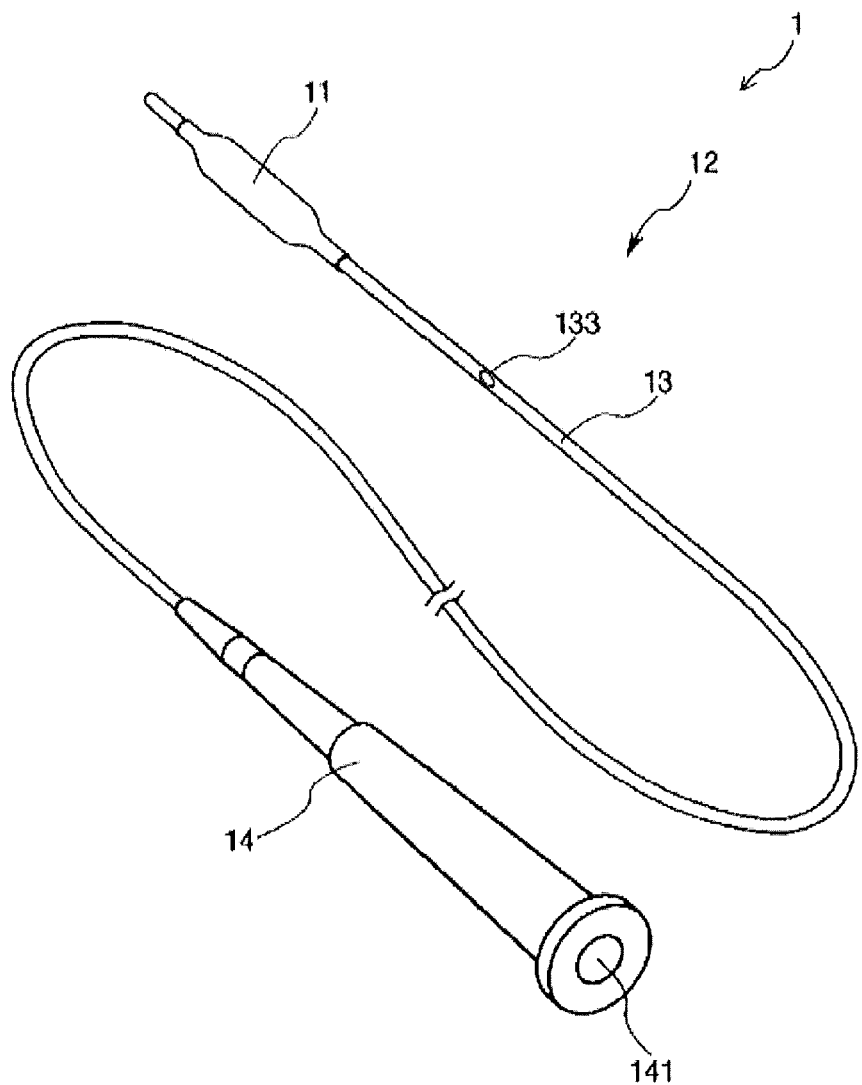
FIG. 1 is a perspective view of one example of a balloon catheter in accordance with the disclosure here, with the balloon expanded.
Figure 2:
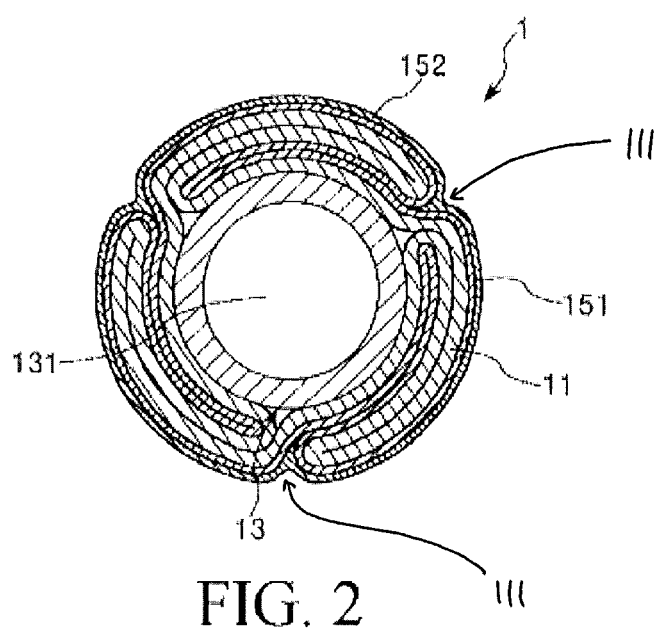
FIG. 2 is a cross-sectional view of the balloon in a folded state.
Figure 3:
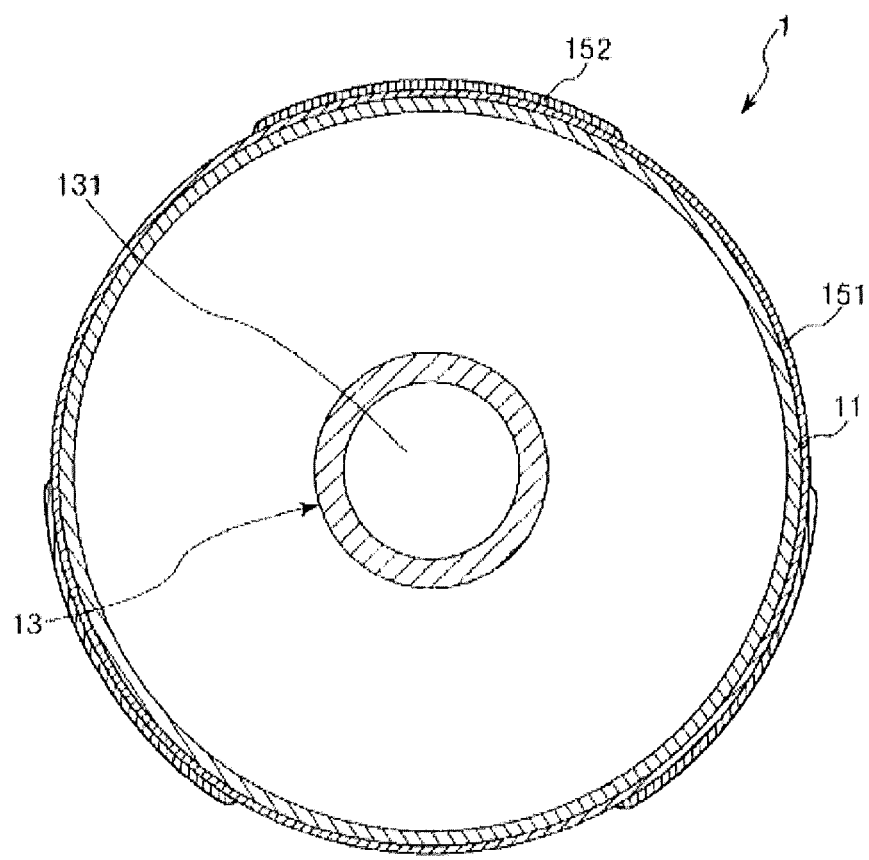
FIG. 3 is a cross-sectional view of the balloon in an expanded state.

FIGS. 1-3 illustrate one example of a balloon catheter in accordance with the disclosure here, as well as the balloon used in the balloon catheter. Features and aspects of the balloon and balloon catheter illustrated in the drawing figures are exaggerated to facilitate an understanding of the disclosure here, and so actual dimensions and the like are not accurately reflected in the drawing figures.

The balloon catheter 1 shown in FIG. 1 as one example of the balloon catheter in accordance with the disclosure here includes an elongated catheter 12, and a balloon 11 disposed on the catheter 12. The catheter 12 includes a catheter body 13 which is flexible, and a hub 14 connected to a proximal end (base end) of the catheter body 13. Thus, the balloon catheter 1 is comprised of the flexible catheter body 13, the hub 14 connected to the proximal end of the catheter body 13, and the balloon 11 at the distal end portion (tip portion) of the catheter body 13. The balloon 11 is firmly attached to the distal portion of the catheter body 13 by, for example, fusing (welding), adhesion or the like.

The intermediate portion of the catheter body 13 is provided with an opening 133 for a guide wire. The catheter body 13 is provided therein with a first lumen 131 which communicates with the opening 133 and opens at the distal end of the catheter 12.

The hub 14 has a port 141 communicating with a second lumen inside the catheter body 13. When a balloon-expanding fluid is injected via the port 141, the fluid is fed into the balloon 11 through the second lumen provided inside the catheter body 13. This increases the internal pressure in the balloon 11 and thus expands the balloon 11. When the balloon-expanding fluid is drawn out of the balloon via the port 141, the fluid is discharged from the inside of the balloon 11 and so the balloon 11 contracts.

When the catheter 12 is in an unused state, the balloon 11 is kept contracted and folded in such a manner as to be wrapped around an outer periphery of the catheter body 13.

In addition, the balloon catheter 1 is provided, at least on the outer surface of the balloon 11, with a hydrophilic coating layer composed of a hydrophilic material. Particularly, the balloon catheter 1 in the present embodiment has, as the hydrophilic coating layer, a first hydrophilic coating layer 151 on the whole outer surface of the balloon 11, and a second hydrophilic coating layer 152 provided so as to surround the periphery of the balloon 11 when the balloon is in the folded state in which the balloon 11 is wrapped around the catheter body 13 as shown in FIG. 2. With the balloon catheter 1 thus having the first hydrophilic coating layer 151 and the second hydrophilic coating layer 152, excellent adhesion exists between the balloon 11 and the hydrophilic coating layer (the first hydrophilic coating layer 151 and the second hydrophilic coating layer 152) composed of the hydrophilic material. As a result, the balloon catheter 1 can be made excellent in durability, and sliding resistance can be kept relatively low even in the case where frictional resistance is exerted repeatedly. When the balloon 11 is in the folded state, a comparatively thick hydrophilic coating layer (a laminate of the first hydrophilic coating layer 151 and the second hydrophilic coating layer 152) is exposed at a part or parts exposed to the outer surface (i.e., exposed to the outside), and a comparatively thin hydrophilic coating layer (the first hydrophilic coating layer 151) is present at a part or parts which are folded to the inside (i.e., not exposed to the outside). This helps ensure that the frictional resistance between portions of the balloon 11 (the frictional resistance between portions of the first hydrophilic coating layer 151) at the part or parts folded to the inside is appropriately high. That is, in the balloon 11 in the folded state, frictional resistance at the part or parts folded to the inside is greater than that at the exposed part or parts of the balloon. As a result, even in the case where a comparatively high frictional force is exerted on the outer surface of the balloon 11 held in the folded state, the balloon 11 is relatively securely prevented from being unfolded or becoming out of shape.

In addition, in the present embodiment, when the balloon 11 is in the folded state, the fold of the balloon 11 overlaps other parts of the balloon 11, and the second hydrophilic coating layer 152 is provided so as to extend across the boundary 111 between the fold and the other part (see FIG. 2). The boundaries 111 are the regions on the outer periphery of the folded balloon between circumferentially adjacent folds as shown in FIG. 2. This helps ensure that when the balloon 11 is in the folded state, the hydrophilic coating layer (the second hydrophilic coating layer 152) provided so as to surround the outer periphery of the folded balloon 11 is continuous. That is, the second hydrophilic coating layer 152 covers the boundaries 111 so that the second hydrophilic coating layer 152 forms an uninterrupted (circumferentially continuous) outer coating on the folded balloon spanning the boundaries. As a result, even in the case where a comparatively large external force or the like is exerted, for example, a chance of exfoliation of the hydrophilic coating layer is reduced or eliminated, so that the hydrophilic coating layer is particularly insusceptible to peeling. In other words, the balloon catheter 1 is particularly high in durability and reliability.

The thickness of the first hydrophilic coating layer 151 is preferably smaller than the thickness of the second hydrophilic coating layer 152. This helps enable the balloon catheter 1 to be especially excellent in durability. Consequently, low sliding resistance can be maintained over a longer period of time, even in the case where frictional resistance is repeatedly exerted on the balloon catheter 1.

Examples of the hydrophilic material (hydrophilic coating material) constituting the hydrophilic coating layer (the first hydrophilic coating layer 151 and the second hydrophilic coating layer 152) include cellulose polymers, polyethylene oxide polymers, maleic anhydride polymers (for example, maleic anhydride copolymers such as methyl vinyl ether-maleic anhydride copolymer), acrylamide polymers (for example, polyacrylamide, polyglycidyl methacrylate-dimethylacrylamide (PGMA-DMAA) block copolymer), water-soluble nylons, polyvinyl alcohol, and polyvinylpyrrolidone.

Incidentally, while it suffices for the hydrophilic coating layer to be provided at least on the outer surface of the balloon 11, it is preferable for the hydrophilic coating layer to also be provided on the outer surface of the catheter body 13.

An example of method of manufacturing the above-described balloon catheter 1 in accordance with the disclosure here is now set forth.

Referring to FIG. 4, the balloon catheter 1 described above can be manufactured by a method that generally includes: a first application step (1a) involving applying a first application liquid 2 containing a hydrophilic coating material to the outer periphery of a balloon 11 which is disposed on a catheter 12 and is held in an expanded state; a cleaning step (1b) involving cleaning the part of the balloon coated with the first application liquid 2 through use of a cleaning liquid 4 while the balloon 11 is expanded; a folding step (1c) involving folding the balloon 11; a heating step (1d) in which the balloon catheter 1 is mounted to a tube 9 for maintaining the folded state of the balloon 11, with the balloon 11 in this state then being subjected to a heating treatment; a second application step (1e) involving applying a second application liquid 3, which contains a hydrophilic coating material, to the balloon 11 while the balloon 11 is folded; and a containing step (1f) involving containing the balloon 11 in the folded state, into a protective case (protective sheath) 8. Each of these steps is described below in more detail.

<First Application Step>

This step may be any one which is carried out by applying the first application liquid 2, which contains the hydrophilic coating material, to the balloon 11 which is disposed on the catheter 12 and which is held in an expanded state. For instance, the first application step can be carried out by a method selected from the group consisting of dipping and spraying. In the present embodiment, among the above-mentioned methods, dipping is used. Specifically, in the present embodiment, the first application step is carried out by dipping the entire balloon 11, in an expanded state and mounted on the catheter, and also dipping at least a part of the catheter body 13, in the first application liquid 2 contained in a tank 5 as shown in 1a of FIG. 4. Adopting this aspect of the method helps ensure that, even where the first hydrophilic coating layer 151 to be formed is comparatively large in thickness, unintentional scattering of film thickness can be reliably inhibited or prevented from occurring, and productivity of the balloon catheter 1 can be made particularly excellent.

The first application liquid 2 normally contains a solvent, in addition to the hydrophilic coating material (hydrophilic material). By utilizing this, conditions such as viscosity of the first application liquid 2 are regulated to preferable values.

Examples of the solvent used in the first application liquid 2 include tetrahydrofuran (THF), dimethylformamide (DMF), and isopropyl alcohol (IPA).

The content of the hydrophilic coating material (hydrophilic material) in the first application liquid 2 is not particularly limited, but is preferably 0.1 to 10 wt %, more preferably 0.1 to 5 wt %. This contributes to the first hydrophilic coating layer 151 having a comparatively small thickness, while securely inhibiting or preventing unintentional scattering of film thickness from occurring. In addition, when the content of the hydrophilic coating material (hydrophilic material) in the first application liquid 2 is in the above-mentioned range, the first hydrophilic coating layer 151 can be formed to have minute ruggedness (minute projections and recesses) on its outer surface. As a result, in the folded state of the balloon 11, the area of contact between portions of the surface of the balloon 11 folded to the inside (the surface where the hydrophilic coating layer is provided) is reduced, and so undesirable adhesion (blocking) or the like can be relatively securely prevented. The final balloon is thus not so susceptible to potential problems at the time of expansion of the balloon 11. That is, the possibility of portions of the balloon sticking to one another in a way that would inhibit or prevent the balloon from expanding in the desired manner is avoided.

When dipping is used to apply the hydrophilic coating material to the balloon, after the balloon (and at least a part of the catheter body 13) is dipped into the first application liquid 2 in the tank 5, the coated balloon is then pulled out of the liquid 2 in the tank 5. The rate of pulling up the balloon 11 from the first application liquid 2 is preferably 1 to 20 mm/sec, more preferably 1.67 to 16.7 mm/sec. This rate helps ensure that the first hydrophilic coating layer 151 with a comparatively large thickness is formed on the balloon, while relatively securely preventing unintentional scattering of film thickness from occurring. When the rate of pulling up the balloon 11 is in the above-mentioned range, the first hydrophilic coating layer 151 can be formed to have the minute ruggedness (minute projections and recesses) on its surface as mentioned above. Consequently, in the folded state of the balloon 11, the area of contact between portions of the surface of the balloon 11 folded to the inside (the surface where the hydrophilic coating layer is provided) is reduced, and generation of undesirable adhesion (blocking) or the like can be fairly reliably avoided or prevented. Accordingly, as mentioned above, in the balloon catheter 11 obtained finally, generation of troubles at the time of expansion of the balloon 11 or the like can be more reliably avoided or prevented.

<Cleaning Step>

Following the first application step, with the balloon 11 held in an expanded state, the part coated with the first application liquid 2 is cleaned by use of the cleaning liquid 4 generally shown at 1b in FIG. 4. This helps ensure that, for example, unintentional scattering of the thickness of the coating film formed from the first application liquid 2 applied onto the balloon 11 is reduced, and smoothness can be enhanced appropriately.

This cleaning of the balloon can be carried out by use of a method selected from the group consisting of dipping into the cleaning liquid and spraying of the cleaning liquid. In the present embodiment, dipping is adopted. Specifically, in the present embodiment, this step is carried out by dipping the part coated with the first application liquid 2 (the whole part of the balloon 11 and at least a part of the catheter body 13) in the cleaning liquid while keeping the balloon 11 in the expanded state as shown at (1b) in FIG. 4. Adoption of such a method makes it possible to relatively assuredly obtain the above-mentioned beneficial results.

<Folding Step>

Next, the balloon 11 is folded in such a manner as to be wrapped around the outer periphery of the catheter body 13 as generally illustrated in 1c of FIG. 4. In the configuration shown in the drawing, the parts which are folded are three parts. But the parts which are folded may be two parts or may be four or more parts.

<Heating Step>

Subsequently, the catheter body 13 with the balloon 11 thereon is mounted in the tube 9 for maintaining the folded state of the balloon 11, and the balloon 11 in this state is subjected to heating treatment as depicted in 1d of FIG. 4. This helps ensure that the shape and other aspects or attributes of the first hydrophilic coating layer 151 formed from the first application liquid 2 are stabilized. This also helps ensure that, for example, the adhesion of the first hydrophilic coating layer 151 to the balloon 11 is quite good. In addition, carrying out this step helps impart a folding tendency to the balloon 11, whereby the balloon can be relatively securely prevented from being unintentionally unfolded as at the time of inserting the finally obtained balloon catheter 1 into a blood vessel or during subsequent manufacturing processes of the balloon catheter 1 (for example, during a second application step to be described later).

<Second Application Step>

Next, the tube 9 is removed, and, while maintaining the balloon 11 in the state in which it is folded, application of the second application liquid 3 containing a hydrophilic coating material is performed as shown at 1e in FIG. 4.

Thus, the first application step in which the first application liquid containing a hydrophilic coating material is applied to the outer periphery of the balloon held in the expanded state, and the second application step in which application of the second application liquid containing a hydrophilic coating material is conducted with the balloon held in the folded state, are both carried out. This helps ensure that adhesion between the hydrophilic coating and the balloon is excellent, and the balloon catheter exhibits quite excellent durability, so that even in the case where frictional resistance is exerted repeatedly, the sliding resistance can be kept relatively low.

In a case where application of the application liquid containing a hydrophilic coating material is conducted only with the balloon expanded or in the case where the application of the application liquid is conducted only with the balloon folded, the above-mentioned excellent effects cannot be obtained.

Particularly in the case where the application of the application liquid containing a hydrophilic coating material is conducted only with the balloon folded, the adhesion between the balloon and the hydrophilic coating layer is insufficient, so that troubles such as exfoliation of a part of the hydrophilic coating layer upon expansion of the balloon are liable to occur. In the case where the application of the application liquid containing a hydrophilic coating material is conducted only with the balloon folded, the balloon catheter obtained would have a problem in that, when a comparatively large frictional force is exerted on the outer surface of the balloon in the folded state, such troubles as unfolding of the balloon or the balloon getting out of shape are more liable to occur than in the case where the first application step is also conducted.

In addition, in the case where the application of the application liquid containing a hydrophilic coating material is performed only with the balloon expanded, the hydrophilic coating layer may be peeled at the time of folding the balloon. In addition, undesirable adhesion (blocking) or the like is liable to occur in the folded state of the balloon, resulting in the possibility of a degraded operationality at the time of expanding the balloon, and unintentional deformation of the balloon may occur when the balloon is expanded. It might be thought that the above-noted problems can be addressed by reducing the amount of the hydrophilic coating material applied to the balloon. But, in that case, it would not be possible to sufficiently obtain the effect of provision of the hydrophilic coating layer.

The second application step can be carried out, for example, by a method selected from the group consisting of dipping and spraying. Among the above-mentioned methods, dipping is adopted in the present embodiment. Thus, in the present embodiment, the second application step is carried out by dipping the whole part of the balloon 11 in the folded state and at least a part of the catheter body 13 in the second application liquid 3 contained in a tank 6 (see (1e) of FIG. 4). With such a method adopted, it is ensured that unintentional scattering of film thickness can be securely prevented from occurring in regard of the second hydrophilic coating layer 152 obtained, and productivity of the balloon catheter 1 can be made particularly excellent.

The second application liquid 3 normally contains a solvent, in addition to the hydrophilic coating material (hydrophilic material). By this, such conditions as viscosity of the second application liquid 3 are controlled to suitable values. As the solvent for constituting the second application liquid 3, there can be used such solvents as mentioned above as examples of the solvent constituting the first application. In this case, the solvent constituting the first application liquid 2 and the solvent constituting the second application liquid 3 may not necessarily have the same composition.

The present step (second application step) is preferably conducted in different conditions from those for the above-mentioned first application step. This helps ensure that, in the state in which the balloon 11 of the finally obtained balloon catheter 1 is folded, the conditions of the hydrophilic coating layers (e.g., thickness, surface roughness, etc.) with respect to the part folded to the inside and the part exposed to the outer periphery, of the outer surface of the balloon 11, can respectively be controlled to suitable values.

Examples of those conditions (application conditions) adopted for the present step (second application step) which are set different from the conditions adopted for the first application step mentioned above include the composition of the application liquid (the composition of the hydrophilic coating material, the composition of the solvent, the content of the hydrophilic coating material, etc.), the rate of pulling-up from the application liquid, and the treatment temperature. In addition, the present step (second application step) may be carried out by an applying method different from that in the first application step mentioned above. For instance, either the first application step or the second application step may be carried out by dipping, and the other application step may be carried out by spraying.

In the present embodiment disclosed by way of example, the second application liquid 3 preferably possesses a higher content of the hydrophilic coating material than the first application liquid 2. This helps ensure that, in the state in which the balloon 11 of the finally obtained balloon catheter 1 is folded, the smoothness of the hydrophilic coating layer provided at that part of the outer surface of the balloon 11 which is exposed to the outer periphery can be reliably made higher than the smoothness of the hydrophilic coating layer provided at that part of the outer surface which is folded to the inside. As a result, sliding resistance at the time of inserting the balloon catheter 1 into a blood vessel can be reduced, and such state can be maintained suitably. Moreover, operationality at the time of expanding the balloon 11 of the balloon catheter 1 to the expanded state is quite excellent.

It is preferable that balloon catheter manufacturing method be implemented to satisfy the relationship $1<X2/X1\leq100$, more preferably to satisfy the relationship $1.5\leq X2/X1\leq50$, where $X1$ [wt %] is the content of the hydrophilic coating material in the first application liquid 2 and $X2$ is the content [wt %] of the hydrophilic coating material in the second application liquid 3. This helps contribute to the above-mentioned effects being exhibited more conspicuously.

The content of the hydrophilic coating material (hydrophilic material) in the second application liquid 3 is not particularly limited. A preferably content is 0.1 to 10 wt %, more preferably 1 to 6 wt %. When the balloon 11 of the balloon catheter 1 is folded, this helps ensure that the film thickness of the hydrophilic coating layer at that part of the outer surface of the balloon 11 which is exposed to the outer periphery (the sum of the film thickness of the first hydrophilic coating layer 151 and the film thickness of the second hydrophilic coating layer 152) is sufficiently large, and the second hydrophilic coating layer 152 is able to exhibit excellent surface smoothness.

In addition, the rate of pulling up the balloon 11 from the second application liquid 3 in the second application step is preferably set higher than the rate of pulling up the balloon 11 from the first application liquid 2 in the first application step. That is, the balloon 11 is pulled up from the second application liquid 3 in the second application step more quickly than the balloon 11 is pulled up from the first application liquid 3 in the first application step. By virtue of this, with the balloon 11 of the finally obtained balloon catheter 1 folded, the smoothness of the hydrophilic coating layer provided at that part of the outer surface of the balloon 11 which is exposed to the outer periphery can be securely made higher than the smoothness of the hydrophilic coating layer provided at that part of the outer surface which is folded to the inside. As a result, sliding resistance at the time of inserting the balloon catheter 1 into a blood vessel can be made lower, and that state can be suitably maintained. Moreover, operationality at the time of expanding the balloon 11 of the balloon catheter 1 to the expanded state is quite excellent.

The balloon catheter manufacturing method is also preferably implemented to satisfy the relationship $1<V2/V1\leq20$, more preferably to satisfy the relationship $1.05\leq V2/V1\leq10$, where V1 [mm/sec] is the rate of pulling up the balloon 11 from the first application liquid and V2 [mm/sec] is the rate of pulling up the balloon 11 from the second application liquid. This contributes to the above-mentioned effects being exhibited more conspicuously.

The rate of pulling up the balloon 11 from the second application liquid 3 is preferably 1 to 20 mm/sec, more preferably 5 to 19 mm/sec. In the state in which the balloon 11 of the balloon catheter 1 is folded, this helps ensure that the film thickness of the hydrophilic coating layer (the sum of the film thickness of the first hydrophilic coating layer 151 and the film thickness of the second hydrophilic coating layer 152) provided at that part of the outer surface of the balloon 11 which is exposed to the outer periphery is sufficiently large, and the second hydrophilic coating layer 152 exhibits particularly excellent surface smoothness.

After the present step (second application step), a drying treatment (e.g., an air-drying treatment) may be carried out to, for example, remove the solvent or the like present on the balloon 11 or the like, prior to the containing step which will be described below.

<Containing Step>

Subsequently, the balloon 11 in the folded state is contained or placed in a protective case (protective sheath) 8 (1f). As a result of this, the desired balloon catheter 1 is obtained.

While an embodiment of the balloon, balloon catheter and method of manufacture have been described above, the invention is not limited to such embodiment.

For instance, the configuration of each of the components of the balloon catheter can be replaced with an arbitrary configuration that can exhibit the same or similar function. And other features and/or aspects may be added.

In addition, while the first application step and the second application step have been described to be each carried out once in the above embodiment, the first application step and/or the second application step may be carried out two or more times. For instance, a process may be adopted in which the first application step is conducted a plurality of times, thereafter the folding step is performed, and then the second application step is further carried out a plurality of times. In addition, a series of steps including the first application step, the folding step and the second application step may be repeated a plurality of times.

The description set forth above explains that the first application step and the second application step are conducted under different conditions. But the first application step and the second application step may be carried out under the same conditions. In addition, the description above explains that the content of the hydrophilic coating material in the first application liquid used in the first application step is lower than the content of the hydrophilic coating material in the second application liquid used in the second application step, and the rate of pulling up the balloon from the first application liquid in the first application step is lower than the rate of pulling up the balloon from the second application liquid in the second application step. However, the combination of the conditions for the first application step with the conditions for the second application step is not restricted to the above-mentioned combination. In this case, an effect or effects according to the combination of the conditions are obtained.

EXAMPLES

Now, specific examples of the present invention will be described below.

[1] Manufacture of Balloon Catheter

Example 1

First, a balloon formed from a polyamide elastomer was prepared. The balloon was joined to a tip (distal) portion of a catheter body formed from a polyamide elastomer by fusing (welding), and a hub was connected to the base end (proximal end) of the catheter body.

Next, with the balloon expanded, immersion (dipping) of the whole part of the balloon (i.e., the entire balloon was immersed or dipped) and a part of the catheter body in a first application liquid containing a hydrophilic coating material was conducted, thereby to apply the first application liquid to these parts (first application step). The first application liquid used here was composed of a dimethylacrylamide (DMAA)-glycerol methacrylate (GMA) copolymer as the hydrophilic coating material and tetrahydrofuran (THF) as a solvent. The content X1 of the hydrophilic coating material in the first application liquid was 1.5 wt %. In addition, the rate V1 of pulling up the balloon from the first application liquid was 13.3 mm/sec.

Next, with the balloon expanded, the whole part of the balloon and a part of the catheter body were immersed in water used as a cleaning liquid, and the parts coated with the first application liquid were cleaned (cleaning step).

Thereafter, the parts to which the first application liquid and the cleaning liquid were applied were air-dried, and the balloon was wrapped around the outer periphery of the catheter body (folding step).

Subsequently, a plastic-made tube was mounted on the outer periphery of the balloon thus folded, so as to maintain the folded state of the balloon, and, in this state, the folded balloon on the tube was subjected to a heating treatment (heating step).

Next, the tube was removed, and, in that state (the state in which the balloon was folded), immersion (dipping) of the whole part of the balloon (i.e., the entire balloon was immersed or dipped) and a part of the catheter body in a second application liquid containing a hydrophilic coating material was performed, thereby to apply the second application liquid to these parts (second application step). The second application liquid used here was composed of dimethylacrylamide (DMAA)-glycerol methacrylate (GMA) copolymer as the hydrophilic coating material and tetrahydrofuran (THF) as a solvent. The content X2 of the hydrophilic coating material in the second application liquid was 1.5 wt %. In addition, the rate V2 of pulling up the balloon from the second application liquid was 13.3 mm/sec.

Thereafter, the parts to which the second application liquid was applied were air-dried, and the balloon in the folded state was contained into or placed in a plastic-made protective case (protective sheath), thereby to obtain the desired balloon catheter (containing step).

Example 2

A balloon catheter was manufactured in the same manner as in Example 1, except that in the second application step an application liquid having a content X2 of the hydrophilic coating material of 3.0 wt % was used as the second application liquid and the rate V2 of pulling up the balloon from the second application liquid was 15.0 mm/sec.

Comparative Example 1

A balloon catheter was manufactured in the same manner as in Example 1, except that the second application step was omitted. Specifically, in this comparative example, application of the hydrophilic coating material was conducted only with the balloon expanded, and application of the hydrophilic coating material was not performed with the balloon folded.

Comparative Example 2

A balloon catheter was manufactured in the same manner as in Example 1, except that the first application step, the cleaning step and the heating step were omitted. Specifically, in this comparative example, application of the hydrophilic coating material was conducted only with the balloon folded, and application of the hydrophilic coating material was not carried out with the balloon expanded.

[2] Evaluation

For each of the balloon catheters obtained in the Examples and the Comparative Examples above, slidability was evaluated in the following manner.

First, the balloon of each of the balloon catheters obtained in the Examples and the Comparative Examples was immersed in water.

Next, a hole was bored in a silicone valve (made by Dow Corning Corporation; 1 mm in thickness), and a stainless steel wire was passed therethrough.

Next, the balloon catheter was inserted along the stainless steel into the valve body, starting from the distal side of the balloon catheter, and the balloon catheter was so positioned that the boundary between a tapered portion and a straight portion of the balloon made contact with the valve body.

In this state, a sliding test was conducted under the conditions of a velocity of 500 mm/min and a stroke of 10 mm.

The sliding test was performed by a method in which 50 reciprocations were made for one set, the above-mentioned sliding operation was repeated for five sets, and the load acting on the balloon catheter during the sliding was measured on an autograph. The silicone valve body was replaced upon completion of each set.

[2-1] Sliding Resistance at First-Time Sliding in the First Set

For each balloon catheter obtained in the Examples and the Comparative Examples above, the sliding resistance (the load acting on the balloon catheter) at the time of the first-time sliding in the first set was determined, and evaluation thereof was conducted according to the following criterion.

A: Sliding resistance (the load acting on the balloon catheter) is less than 10 gf
B: Sliding resistance (the load acting on the balloon catheter) is not less than 10 gf and less than 12 gf
C: Sliding resistance (the load acting on the balloon catheter) is not less than 12 gf and less than 14 gf
D: Sliding resistance (the load acting on the balloon catheter) is not less than 14 gf

[2-2] Increment in Sliding Resistance

For each of the balloon catheters obtained in the Examples and the Comparative Examples above, the difference between the sliding resistance (the load acting on the balloon catheter) at the time of the final-time sliding in the fifth set and the sliding resistance (the load acting on the balloon catheter) at the time of the first-time sliding in the first set (the increment in sliding resistance) was determined, and evaluation thereof was conducted according to the following criterion.

A: Increment in sliding resistance is less than 7 gf
B: Increment in sliding resistance is not less than 7 gf and less than 15 gf
C: Increment in sliding resistance is not less than 15 gf and less than 40 gf
D: Increment in sliding resistance is not less than 40 gf The results of the evaluations above are shown in Table 1.

TABLE 1

|  | Sliding resistance at first-time sliding in first set | Increment in sliding resistance |
|---|---|---|
| Example 1 | A | A |
| Example 2 | A | A |
| Comparative Example 1 | A | D |
| Comparative Example 2 | B | D |

The results in Table 1 show that in each of the Examples utilizing the balloon catheter and manufacturing method disclosed here, the sliding resistance of the balloon was kept low even when a frictional resistance was exerted repeatedly, indicating that the balloon catheter exhibits excellent durability. In contrast, in the Comparative Examples, the sliding resistance rose greatly when a frictional resistance was exerted repeatedly, indicating that the balloon catheter possesses poor durability.

The method of manufacturing a balloon catheter according to the disclosure here includes: applying a first application liquid, which contains a hydrophilic coating material, to the outer periphery of a balloon which is disposed on a catheter and is held in an expanded state; folding the balloon; and applying a second application liquid, which contains a hydrophilic coating material, to the balloon with the balloon folded. Therefore, it is possible to provide a method of manufacturing a balloon catheter by which the sliding resistance on the balloon is kept low and a balloon catheter excellent in operationality can be suitably manufactured.

The detailed description above describes features, aspects and characteristics of a balloon catheter and method of manufacturing a balloon catheter as disclosed here. The invention is not limited, however, to the precise embodiment and variations described above and illustrated in the drawing figures. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:
1. A balloon catheter comprising:
a catheter that includes a catheter body connectable to a catheter hub:
a balloon disposed on the catheter body, the balloon being contracted and wrapped around the catheter body so that the balloon is folded, with parts of the balloon folded to inside, the folded balloon possessing an outer surface;
a lumen in the catheter in fluid communication with an interior of the balloon to introduce expanding fluid into the balloon;
a first hydrophilic coating layer, including a first polymer, on an outer surface of the balloon, the first hydrophilic coating layer existing on the outer surface including the outer surface of the parts of the balloon folded to the inside; and
a second hydrophilic coating layer, including a polymer that is identical with said first polymer, in contact with a portion of the first hydrophilic coating layer and continuously surrounding an outer periphery of the folded balloon including portions of the outer periphery of the balloon at which the first hydrophilic coating layer exists.

2. The balloon catheter according to claim 1, wherein the first hydrophilic coating layer and the second hydrophilic coating layer possess different compositions.

3. The balloon catheter according to claim 1, wherein the second hydrophilic coating layer is present only at spaced apart locations on an outer surface of the balloon when the balloon is expanded.

4. The balloon catheter according to claim 1, wherein the thickness of the first hydrophilic coating layer is smaller than the thickness of the second hydrophilic coating layer.

5. A balloon catheter comprising:
   a catheter;
   a balloon disposed on the catheter and folded on the catheter so that the balloon is wrapped around the catheter;
   a first hydrophilic coating layer, including a first polymer, on an outer surface of the balloon;
   a second hydrophilic coating layer, including a polymer that is identical with said first polymer, in contact with a portion of the first hydrophilic coating layer and surrounding an outer periphery of the balloon in the state of being folded in such a manner as to be wrapped around the catheter.

6. The balloon catheter according to claim 5, wherein a fold of the folded balloon overlaps an other part of the balloon, and the second hydrophilic coating layer extends across a boundary between the fold and the other part and into a gap defined by the fold and the other part.

7. The balloon catheter according to claim 5, wherein the thickness of the first hydrophilic coating layer is smaller than the thickness of the second hydrophilic coating layer.

8. The balloon catheter according to claim 5, wherein the first hydrophilic coating layer and the second hydrophilic coating layer possess different compositions.

9. The balloon catheter according to claim 5, wherein the second hydrophilic coating layer is present only at spaced apart locations on the outer surface of the balloon when the balloon is expanded.

10. The balloon catheter according to claim 1, wherein a fold of the folded balloon overlaps an other part of the balloon, and the second hydrophilic coating layer extends across a boundary between the fold and the other part and into a gap defined by the fold and the other part.

11. The balloon catheter according to claim 1, wherein the first hydrophilic coating layer and the second hydrophilic coating layer are provided on a portion of the catheter body.

12. The balloon catheter according to claim 5, wherein the first hydrophilic coating layer and the second hydrophilic coating layer are provided on a portion of the catheter.

* * * * *